US011793813B2

(12) United States Patent
Chen et al.

(10) Patent No.: US 11,793,813 B2
(45) Date of Patent: *Oct. 24, 2023

(54) PEMETREXED FORMULATIONS

(71) Applicant: Eagle Pharmaceuticals, Inc., Woodcliff Lake, NJ (US)

(72) Inventors: Feng-Jing Chen, Irvine, CA (US); Steven L Krill, Midland Park, NJ (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,236

(22) Filed: Jun. 8, 2022

(65) Prior Publication Data

US 2022/0296603 A1 Sep. 22, 2022

Related U.S. Application Data

(63) Continuation of application No. 16/297,125, filed on Mar. 8, 2019, which is a continuation of application No. 15/828,858, filed on Dec. 1, 2017, now abandoned, which is a continuation of application No. 15/048,416, filed on Feb. 19, 2016, now abandoned.

(51) Int. Cl.
| *A61K 31/519* | (2006.01) |
| *A61K 9/00* | (2006.01) |
| *A61K 47/02* | (2006.01) |
| *A61K 47/10* | (2017.01) |

(52) U.S. Cl.
CPC .......... *A61K 31/519* (2013.01); *A61K 9/0019* (2013.01); *A61K 47/02* (2013.01); *A61K 47/10* (2013.01)

(58) Field of Classification Search
CPC .... A61K 31/519; A61K 9/0019; A61K 47/02; A61K 47/10
See application file for complete search history.

(56) References Cited

U.S. PATENT DOCUMENTS

| 4,931,441 A | 6/1990 | Lawrence |
| 6,087,393 A | 7/2000 | Mathur |
| 6,686,365 B2 | 2/2004 | Riebesehl et al. |
| 8,796,265 B2 | 8/2014 | Moreau |
| 9,364,433 B2 | 6/2016 | Andersson et al. |
| 9,421,207 B2 | 8/2016 | Khattar et al. |
| 9,655,898 B2 | 5/2017 | Palepu |
| 2007/0099866 A1 | 5/2007 | Moser et al. |
| 2007/0203173 A1 | 8/2007 | Mudumba et al. |
| 2008/0139810 A1 | 6/2008 | Busolli et al. |
| 2009/0181990 A1* | 7/2009 | Patel .................... C07D 487/04 435/375 |
| 2009/0324552 A1 | 12/2009 | Lichter et al. |
| 2013/0231357 A1* | 9/2013 | Palepu .................... A61K 9/08 514/265.1 |
| 2015/0073000 A1 | 3/2015 | Khattar et al. |
| 2015/0111905 A1* | 4/2015 | Khattar .................. A61K 47/18 514/265.1 |
| 2016/0051679 A1 | 2/2016 | Rotaru |
| 2016/0143911 A1 | 5/2016 | Zaludek et al. |
| 2016/0168153 A1 | 6/2016 | Nadgoud et al. |
| 2017/0239250 A1 | 8/2017 | Chen et al. |
| 2018/0289710 A1 | 10/2018 | Chen et al. |
| 2019/0201405 A1* | 7/2019 | Chen ..................... A61K 47/10 |
| 2020/0246263 A1 | 8/2020 | Khattar et al. |
| 2022/0211709 A1 | 7/2022 | Nayani et al. |
| 2022/0409623 A1 | 12/2022 | Chen et al. |
| 2022/0409624 A1 | 12/2022 | Chen et al. |

FOREIGN PATENT DOCUMENTS

| CN | 1552713 A | 12/2004 |
| CN | 101081305 A | 12/2007 |
| CN | 104098573 A | 10/2014 |
| DE | 102012010774 A1 | 12/2013 |
| EP | 2666463 A1 | 11/2013 |
| IN | 4324/CHE/2015 | 2/2017 |
| JP | 2000-336041 A | 12/2000 |
| JP | 2003-055247 | 2/2003 |
| JP | 2003-521518 A | 7/2003 |
| JP | 2008-543976 A | 12/2008 |
| JP | 2009-523840 A | 6/2009 |
| JP | 2010-043068 A | 2/2010 |
| JP | 2013-540104 A | 10/2013 |
| JP | 2014-513094 A | 5/2014 |
| JP | 2015-127300 A | 7/2015 |
| WO | 00/55416 A1 | 9/2000 |
| WO | 01/56575 A1 | 8/2001 |
| WO | WO-2007023243 A2 * | 3/2007 ........... A61K 31/505 |

(Continued)

OTHER PUBLICATIONS

International Search Report, PCT appl. No. PCT/US2016/018703, 2 pages (dated Apr. 29, 2016).
Written Opinion of the International Searching Authority, PCT appl. No. PCT/US2016/018703, 8 pages (dated Apr. 29, 2016).
Alimta (pemetrexed disodium) Injection, Powder, Lyophilized, For Solution for Intravenous use, FDA Prescribing Information, 2008.
Chen et al., U.S. Appl. No. 17/898,558, filed Aug. 30, 2022.
International Search Report and Written Opinion issued in PCT/US2011/045341 dated Dec. 16, 2011.

(Continued)

*Primary Examiner* — Abigail Vanhorn

(74) *Attorney, Agent, or Firm* — COOLEY LLP; Ivor R. Elrifi; Heidi A. Erlacher

(57) ABSTRACT

The present invention is directed to pemetrexed formulations comprising a non-aqueous solvent that remains stable after dilution for at least about 48 hours when stored at 2° C. to 8° C. The present invention is also directed to pemetrexed formulations comprising a non-aqueous solvent that remains stable for at least about 24 months when stored at 2° C. to 8° C.

9 Claims, 2 Drawing Sheets

(56) References Cited

FOREIGN PATENT DOCUMENTS

| WO | 2008/045410 | | 4/2008 |
|---|---|---|---|
| WO | 2010/030598 | | 3/2010 |
| WO | 2012/015810 | A2 | 2/2012 |
| WO | 2013/144814 | A1 | 10/2013 |
| WO | 2013/179248 | A1 | 12/2013 |
| WO | 2013/179310 | A1 | 12/2013 |
| WO | 2014/167585 | A1 | 10/2014 |
| WO | 2014/198337 | A1 | 12/2014 |
| WO | 2015/008221 | A1 | 1/2015 |
| WO | 2015/092758 | A1 | 6/2015 |
| WO | 2015/102315 | A1 | 9/2015 |
| WO | 2015/193517 | A2 | 12/2015 |
| WO | 2016/129000 | A1 | 8/2016 |

OTHER PUBLICATIONS

Anonymously, "Pemetrexed Tromethamine Salts and Its Solid State Forms Thereof, An IP.com Prior Art Database Technical Disclosure," Published May 7, 2014; retrieved from the Internet on Sep. 5, 2018 at http://null/IPCOM/000236645, 26 pages.

Butler et al., "Removal of Dissolved Oxygen from Water: A Comparison of Four Common Techniques," Talanta 41(2):211-215 (1994).

Chen et al., U.S. Appl. No. 17/898,637, filed Aug. 30, 2022.

Chen et al., U.S. Appl. No. 17/898,984, filed Aug. 30, 2022.

\* cited by examiner

PEMETREXED FORMULATIONS

CROSS REFERENCES TO RELATED APPLICATIONS

This application is a continuation of U.S. patent application Ser. No. 16/297,125, filed Mar. 8, 2019, which is a continuation of U.S. patent application Ser. No. 15/828,858, filed Dec. 1, 2017, now abandoned, which is a continuation of U.S. patent application Ser. No. 15/048,416, now abandoned, filed Feb. 19, 2016, the disclosure of each of which is hereby incorporated by reference in its entirety.

BACKGROUND OF THE INVENTION

Compounds exhibiting anti-folate activity have a well known role as chemotherapeutic agents. One such compound is pemetrexed, which has the chemical name N-[4-[2-(2-amino-4,7-dihydro-4-oxo-1H-pyrrolo [2,3-d]pyrimidin-5-yl)ethyl]benzoyl]-L-glutamic acid and the structure of formula (1):

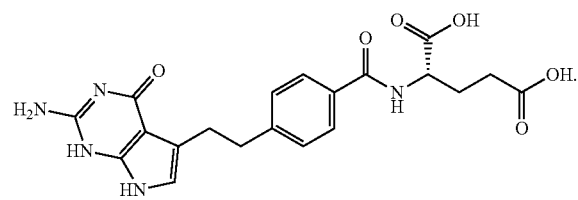 [SMILES: Nc1nc(=O)c2c(CCc3ccc(C(=O)N[C@@H](CCC(=O)O)C(=O)O)cc3)c[nH]c2[nH]1]

Pemetrexed is used in the treatment of pleural mesothelioma and non-small cell lung cancer. ALIMTA, Eli Lilly's pemetrexed product is presently supplied in 100 mg and 500 mg vials of lyophilized pemetrexed disodium for injection. According to the prescribing information, in order to prepare ALIMTA for infusion the vials are reconstituted in sufficient 0.9% Sodium Chloride Injection (preservative free) to give a solution containing 25 mg/mL of ALIMTA. This concentrated solution is then further diluted into a solution of 0.9% Sodium Chloride Injection (preservative free). The prescribing information cautions that reconstitution and further dilution is only recommended with 0.9% Sodium Chloride Injection (preservative free), and that "ALIMTA is physically incompatible with diluents containing calcium, including Lactated Ringer's Injection, USP and Ringer's Injection, USP and therefore these should not be used."

Calcium containing diluents, such as Lactated Ringer's Injection and Ringer's Injection, are common solutions used in medical settings for the reconstitution and/or dilution of drug products prior to intravenous administration. There is a need for pemetrexed dosage forms that are chemically stable after reconstitution and/or dilution with diluents containing calcium. In addition to being useful with a wider range of available diluents, the use of such a dosage form would minimize both the loss of dosage forms due to improper reconstitution or dilution and the risk that a patient would be administered pemetrexed reconstituted or diluted in an incompatible diluent.

In solution, pemetrexed undergoes hydrolysis and degrades rapidly. Due to this rapid degradation, pemetrexed formulations must either be lyophilized for long term stability or comprise stabilizers. However, reconstitution of a lyophilized formulation requires multiple steps, each of which increases the risk of user error. In addition, reconstitution of a lyophilized formulation is clinically inconvenient and can take up to 30 minutes.

While stable, ready to use formulations of pemetrexed are known, they require stabilizers, such as anti-oxidants or amino acids as described in U.S. Pat. No. 6,686,365; CN 101081305; and WO2012015810, or high levels of non-aqueous solvents, as described in WO2013144814. It would be advantageous to minimize patient exposure to these additional ingredients.

As such, there is a need for a stable, non-lyophilized pemetrexed composition with a minimal amount of additional ingredients. To this end, we have developed a stable pemetrexed formulation.

SUMMARY OF THE INVENTION

In certain embodiments, the invention is directed to a pharmaceutical composition comprising pemetrexed and a non-aqueous solvent present at a concentration less than 0.30 ml/mL, wherein upon dilution with a pharmaceutically acceptable diluent to an initial dosage concentration of pemetrexed, the composition comprises at least 90% of the initial dosage concentration of pemetrexed after storage at a temperature of 2° C. to 8° C. for at least 24 hours.

In further embodiments, the invention is directed to a pharmaceutical composition comprising 25 mg/mL pemetrexed, 250 µL/mL propylene glycol, and water, wherein upon dilution with a pharmaceutically acceptable diluent to an initial dosage concentration of pemetrexed, the composition comprises at least 90% of the initial dosage concentration of pemetrexed after storage at a temperature of 2° C. to 8° C. for at least 24 hours.

In still further embodiments, the invention is directed to a pharmaceutical composition comprising pemetrexed at an initial concentration of 10 to 50 mg/mL and a non-aqueous solvent present at a concentration less than 0.30 ml/mL, wherein the composition comprises at least 90% of the initial pemetrexed concentration after storage at a temperature of 2° C. to 8° C. for at least 12 months.

In further embodiments, the invention is directed to a pharmaceutical composition comprising 25 mg/mL pemetrexed, 250 µL/mL propylene glycol, and water, wherein the composition comprises at least 90% of the initial pemetrexed concentration after storage at a temperature of 2° C. to 8° C. for at least 12 months.

In certain embodiments, the invention is directed to a pharmaceutical composition comprising pemetrexed and a non-aqueous solvent present at a concentration less than 0.30 ml/mL, wherein upon dilution with a pharmaceutically acceptable diluent to an initial dosage concentration of pemetrexed, the composition comprises no more than 8% w/w total impurities after storage at a temperature of 2° C. to 8° C. for at least 24 hours.

In further embodiments, the invention is directed to a pharmaceutical composition comprising 25 mg/mL pemetrexed, 250 µL/mL propylene glycol, and water, wherein upon dilution with a pharmaceutically acceptable diluent to an initial dosage concentration of pemetrexed, the composition comprises no more than 8% w/w total impurities after storage at a temperature of 2° C. to 8° C. for at least 24 hours.

In still further embodiments, the invention is directed to a pharmaceutical composition comprising pemetrexed at an initial concentration of 10 to 50 mg/mL and a non-aqueous solvent present at a concentration less than 0.30 ml/mL, the composition comprises no more than 8% w/w total impurities after storage at a temperature of 2° C. to 8° C. for at least 24 hours.

In further embodiments, the invention is directed to a pharmaceutical composition comprising 25 mg/mL pemetrexed, 250 µL/mL propylene glycol, and water, the composition comprises no more than 8% w/w total impurities after storage at a temperature of 2° C. to 8° C. for at least 24 hours.

Additional embodiments of the invention include:
1. A pharmaceutical composition comprising:
   a) pemetrexed and
   b) a non-aqueous solvent present at less than 0.30 mL/mL;
   wherein upon dilution with a pharmaceutically acceptable diluent to an initial dosage concentration of pemetrexed, the composition comprises at least 90% of the initial dosage concentration of pemetrexed after storage at a temperature of 2° C. to 8° C. for at least 12 hours.
2. The pharmaceutical composition of embodiment 1 wherein the composition retains at least 90% of the initial dosage concentration of pemetrexed upon dilution and storage for a period selected from:
   a) at least 24 hours, and
   b) at least 48 hours.
3. The pharmaceutical composition of embodiment 1 wherein the composition retains at least 95% of the initial dosage concentration of pemetrexed upon dilution and storage for a period selected from:
   a) at least 12 hours,
   b) at least 24 hours, and
   c) at least 48 hours.
4. The pharmaceutical composition of embodiment 1 wherein the composition retains at least 98% of the initial dosage concentration of pemetrexed upon dilution and storage for a period selected from:
   a) at least 12 hours,
   b) at least 24 hours, and
   c) at least 48 hours.
5. The pharmaceutical composition of embodiment 1 wherein the pharmaceutically acceptable diluent is selected from the group consisting of normal saline, water for injection, 5% dextrose in water, Ringer's Injection, and Lactated Ringer's Injection.
6. The pharmaceutical composition of embodiment 1 comprising 10 to 50 mg/mL pemetrexed.
7. The pharmaceutical composition of embodiment 6 comprising 25 mg/mL pemetrexed.
8. The pharmaceutical formulation of embodiment 1 wherein the non-aqueous solvent is selected from the group consisting of propylene glycol, alcohol, polyethylene glycol, or combinations thereof
9. The pharmaceutical formulation of embodiment 8 wherein the non-aqueous solvent is propylene glycol.
10. The pharmaceutical formulation of embodiment 9 wherein propylene glycol is present at 250 µL/mL.
11. The pharmaceutical composition of embodiment 1 comprising at least 0.50 mL/mL water.
12. The pharmaceutical composition of embodiment 1 wherein the pemetrexed is in the form of pemetrexed diacid.
13. The pharmaceutical composition of embodiment 1 wherein the pemetrexed is in the form of pemetrexed disodium.
14. The pharmaceutical composition of embodiment 1 substantially free of an anti-oxidant.
15. A pharmaceutical composition comprising
    a) 25 mg/mL pemetrexed, and
    b) propylene glycol at 250 µL/mL
    c) water
    wherein upon dilution with a pharmaceutically acceptable diluent to an initial dosage concentration of pemetrexed, the composition comprises at least 90% of the initial dosage concentration of pemetrexed after storage at a temperature of 2° C. to 8° C. for at least 24 hours.
16. The pharmaceutical composition of embodiment 15 wherein upon dilution with a pharmaceutically acceptable diluent to an initial dosage concentration of pemetrexed, the composition comprises at least 90% of the initial dosage concentration of pemetrexed after storage at a temperature of 2° C. to 8° C. for at least 48 hours.
17. A pharmaceutical composition comprising:
    a) pemetrexed at an initial concentration of 10 to 50 mg/mL and
    b) a non-aqueous solvent present at less than 0.30 mL/mL,
    wherein the composition comprises at least 90% of the initial pemetrexed concentration after storage at a temperature of 2° C. to 8° C. for at least 12 months.
18. The pharmaceutical composition of embodiment 17 wherein the composition comprises at least 90% of the initial pemetrexed concentration after storage for a period selected from:
    a) at least 18 months, and
    b) at least 24 months.
19. The pharmaceutical composition of embodiment 17 wherein the composition comprises at least 95% of the initial pemetrexed concentration after storage for a period selected from:
    a) at least 12 months,
    b) at least 18 months, and
    c) at least 24 months.
20. The pharmaceutical composition of embodiment 17 wherein the composition comprises at least 98% of the initial pemetrexed concentration after storage for a period selected from:
    a) at least 12 months,
    b) at least 18 months, and
    c) at least 24 months.
21. The pharmaceutical composition of embodiment 17 having an initial pemetrexed concentration of 25 mg/mL.
22. The pharmaceutical formulation of embodiment 17 wherein the non-aqueous solvent is selected from the group consisting of propylene glycol, alcohol, polyethylene glycol, or combinations thereof
23. The pharmaceutical formulation of embodiment 22 wherein the non-aqueous solvent is propylene glycol.
24. The pharmaceutical formulation of embodiment 23 wherein propylene glycol is present at 250 µL/mL.
25. The pharmaceutical composition of embodiment 17 comprising at least 0.50 mL/mL water.
26. The pharmaceutical composition of embodiment 17 wherein the pemetrexed is in the form of pemetrexed diacid.
27. The pharmaceutical composition of embodiment 17 wherein the pemetrexed is in the form of pemetrexed disodium.
28. The pharmaceutical composition of embodiment 17 substantially free of an anti-oxidant.

29. A pharmaceutical composition comprising
   a) an initial pemetrexed concentration of 25 mg/mL,
   b) propylene glycol at 250 µL/mL, and
   c) water;
   wherein the composition comprises at least 90% of the initial pemetrexed concentration after storage at a temperature of 2° C. to 8° C. for at least 12 months.
30. The pharmaceutical composition of embodiment 29 wherein the composition comprises at least 90% of the initial pemetrexed concentration after storage at a temperature of 2° C. to 8° C. for at least 24 months.
31. A pharmaceutical composition comprising:
   a) pemetrexed and
   b) a non-aqueous solvent present at less than 0.30 mL/mL,
   wherein upon dilution with a pharmaceutically acceptable diluent to an initial dosage concentration of pemetrexed the composition comprises no more than 8% w/w total impurities after storage at a temperature of 2° C. to 8° C. for at least 12 hours.
32. The pharmaceutical composition of embodiment 31 wherein the composition comprises no more than 8% w/w total impurities after dilution and storage for a period selected from:
   a) at least 24 hours, and
   b) at least 48 hours.
33. The pharmaceutical composition of embodiment 31 wherein the composition comprises no more than 5% w/w total impurities after dilution and storage for a period selected from:
   a) at least 12 hours,
   b) at least 24 hours, and
   c) at least 48 hours.
34. The pharmaceutical composition of embodiment 31 wherein the composition comprises no more than 2% w/w total impurities after dilution and storage for a period selected from:
   a) at least 12 hours,
   b) at least 24 hours, and
   c) at least 48 hours.
35. The pharmaceutical composition of embodiment 31 wherein the pharmaceutically acceptable diluent is selected from the group consisting of normal saline, water for injection, 5% dextrose in water, Ringer's Injection, and Lactated Ringer's Injection.
36. The pharmaceutical composition of embodiment 31 comprising 10 to 50 mg/mL pemetrexed.
37. The pharmaceutical composition of embodiment 36 comprising 25 mg/mL pemetrexed.
38. The pharmaceutical formulation of embodiment 31 wherein the non-aqueous solvent is selected from the group consisting of propylene glycol, alcohol, polyethylene glycol, or combinations thereof
39. The pharmaceutical formulation of embodiment 38 wherein the non-aqueous solvent is propylene glycol.
40. The pharmaceutical formulation of embodiment 39 wherein propylene glycol is present at 250 µL/mL.
41. The pharmaceutical composition of embodiment 31 comprising at least 0.50 mL/mL water.
42. The pharmaceutical composition of embodiment 31 wherein the pemetrexed is in the form of pemetrexed diacid.
43. The pharmaceutical composition of embodiment 31 wherein the pemetrexed is in the form of pemetrexed disodium.
44. The pharmaceutical composition of embodiment 31 substantially free of an anti-oxidant.
45. A pharmaceutical composition comprising
   a) 25 mg/mL pemetrexed,
   b) propylene glycol at 250 µL/mL, and
   c) water;
   wherein upon dilution with a pharmaceutically acceptable diluent to an initial dosage concentration of pemetrexed the composition comprises no more than 8% w/w total impurities after storage at a temperature of 2° C. to 8° C. for at least 24 hours.
46. The pharmaceutical composition of embodiment 45 wherein upon dilution with a pharmaceutically acceptable diluent to an initial dosage concentration of pemetrexed the composition comprises no more than 8% w/w total impurities after storage at a temperature of 2° C. to 8° C. for at least 48 hours.
47. A pharmaceutical composition comprising:
   a) pemetrexed at an initial concentration of 10 to 50 mg/mL and
   b) a non-aqueous solvent present at less than 0.30 mL/mL,
   wherein the composition comprises no more than 8% w/w total impurities after storage at a temperature of 2° C. to 8° C. for at least 12 months.
48. The pharmaceutical composition of embodiment 47 wherein the composition comprises no more than 8% w/w total impurities after storage for a period selected from:
   a) at least 18 months, and
   b) at least 24 months.
49. The pharmaceutical composition of embodiment 47 wherein the composition comprises no more than 5% w/w total impurities after storage for a period selected from:
   a) at least 12 months,
   b) at least 18 months, and
   c) at least 24 months.
50. The pharmaceutical composition of embodiment 47 wherein the composition comprises no more than 2% w/w total impurities after storage for a period selected from:
   a) at least 12 months,
   b) at least 18 months, and
   c) at least 24 months.
51. The pharmaceutical composition of embodiment 47 comprising 25 mg/mL pemetrexed.
52. The pharmaceutical formulation of embodiment 47 wherein the non-aqueous solvent is selected from the group consisting of propylene glycol, alcohol, polyethylene glycol, or combinations thereof
53. The pharmaceutical formulation of embodiment 52 wherein the non-aqueous solvent is propylene glycol.
54. The pharmaceutical formulation of embodiment 53 wherein propylene glycol is present at 250 µL/mL.
55. The pharmaceutical composition of embodiment 47 comprising at least 0.50 mL/mL water.
56. The pharmaceutical composition of embodiment 47 wherein the pemetrexed is in the form of pemetrexed diacid.
57. The pharmaceutical composition of embodiment 47 wherein the pemetrexed is in the form of pemetrexed disodium.
58. The pharmaceutical composition of embodiment 47 substantially free of an anti-oxidant.
59. A pharmaceutical composition comprising
   a) an initial pemetrexed concentration of 25 mg/mL,
   b) propylene glycol at 250 µL/mL, and
   c) water;

wherein the composition comprises no more than 8% w/w total impurities after storage at a temperature of 2° C. to 8° C. for at least 12 months.

60. The pharmaceutical composition of embodiment 59 wherein the composition comprises no more than 8% w/w total impurities after storage at a temperature of 2° C. to 8° C. for at least 24 months.

DETAILED DESCRIPTION

Figure 1A:
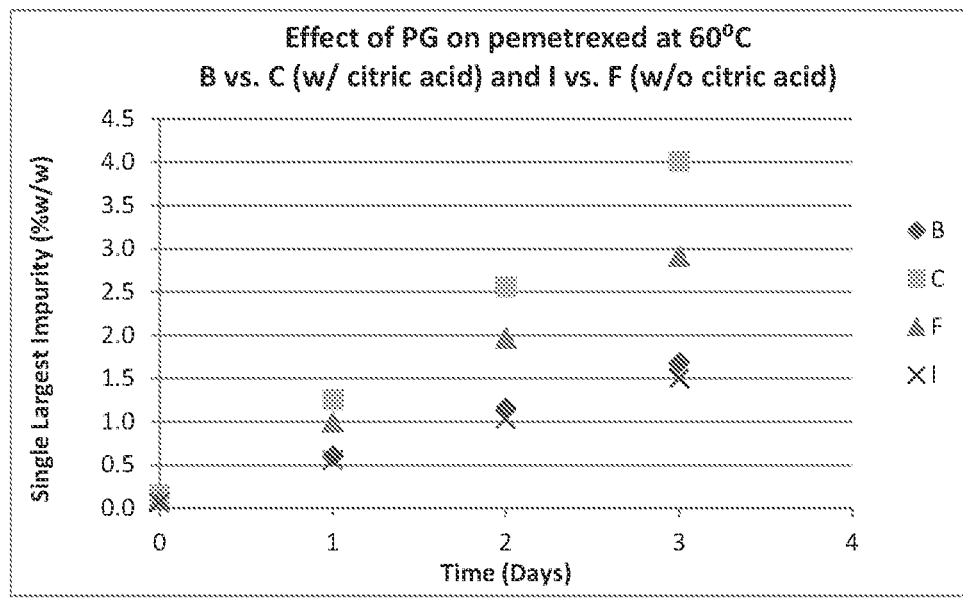
FIGS. 1A-1D: Depicts the effect of propylene glycol (PG) on the stability of certain pemetrexed formulations.

Unless defined otherwise, all technical and scientific terms used herein have the same meaning as is commonly understood by one of ordinary skill in the art to which this invention belongs. In the event that there is a plurality of definitions for a term used herein, those definitions in this section prevail unless stated otherwise.

As used herein "single largest impurity" refers to the impurity with the largest HPLC peak by percentage.

As used herein "initial dosage concentration of pemetrexed" refers to the concentration of pemetrexed at the time of dilution, prior to storage.

As used herein "initial pemetrexed concentration" refers to the concentration of pemetrexed at the time of formulation, prior to dilution and/or storage.

As used herein "room temperature" is about 20° C. to about 25° C.

Pemetrexed or a pharmaceutically acceptable salt thereof is present in the compositions of the present invention at concentrations of between about 10 mg/mL to about 50 mg/mL when calculated as anhydrous pemetrexed diacid. In certain embodiments of the invention, pemetrexed is present at about 10 mg/mL to about 40 mg/mL, at about 10 mg/mL to about 30 mg/mL, at about 10 mg/mL to about 20 mg/mL, at about 20 mg/mL to about 50 mg/mL, at about 20 mg/mL to about 40 mg/mL, at about 20 mg/mL to about 30 mg/mL, at about 30 mg/mL to about 50 mg/mL, at about 30 mg/mL to about 40 mg/mL, or at about 40 mg/mL to about 50 mg/mL. In further embodiments of the invention, pemetrexed is available at about 10 mg/mL, about 15 mg/mL, 20 mg/mL, about 25 mg/mL, about 30 mg/mL, about 35 mg/mL, about 40 mg/mL, about 45 mg/mL, or at about 50 mg/mL.

Pemetrexed is present in the composition as the diacid, monoacid, a pharmaceutically acceptable salt, or as combinations thereof. In certain embodiments of the invention, pemetrexed is present as pemetrexed disodium, in further embodiments of the invention, pemetrexed is present as pemetrexed dipotassium. In yet further embodiments of the invention, pemetrexed is present as pemetrexed meglumine. In still further embodiments of the invention, pemetrexed is present as pemetrexed tromethamine.

Non-Aqueous Solvents

Suitable non-aqueous solvents include, but are not limited to alcohols, ketones, esters, ethers, aromatic hydrocarbons, nitriles, aprotic polar solvents, acidic solvents, and mixtures of any two or more thereof. Useful alcohols include, for example, methanol, ethanol, denatured spirits, n-propanol, isopropanol, n-butanol, isobutanol, t-butanol, polyhydroxy alcohols example glycerin, propylene glycol, polyethylene glycol, diethylene glycol, diglycerin, triethylene glycol, tetraethylene glycol, trimethylolpropane and the like. Useful ketones include propanone, 2-butanone, and the like. Useful esters include, for example, ethyl acetate, n-propyl acetate, isopropyl acetate, n-butyl acetate, t-butyl acetate, and the like. Useful ethers include, for example, dimethyl ether, diethyl ether, methyl t-butyl ether, ethyl methyl ether, diisopropyl ether, and the like. Useful aromatic hydrocarbons include, for example, and the like. Useful nitriles include acetonitrile, propionitrile, and the like. Useful aprotic polar solvents include N,N-dimethylformide (DMF), dimethylsulfoxide (DMSO), N,N-dimethylacetamide (DMA), and the like.

In certain embodiments of the invention, the non-aqueous solvent is an alcohol. In further embodiments of the invention, the non-aqueous solvent is a polyhydroxy alcohol. In still further embodiments of the invention, the non-aqueous solvent is propylene glycol. In yet further embodiments of the invention, the non-aqueous solvent is polyethylene glycol. In particular embodiments of the invention, the non-aqueous solvent is low molecular weight polyethylene glycol. In other embodiments of the invention, the non-aqueous solvent is selected from the group consisting of polyethylene glycol 200, polyethylene glycol 300, polyethylene glycol 400, or combinations thereof. In certain embodiments of the invention, more than one non-aqueous solvent is present, such as, but not limited to polyethylene glycol and propylene glycol.

In certain embodiments of the invention, the non-aqueous solvent is present at a concentration of about 50 mg/mL to 300 mg/mL prior to dilution. In further embodiments of the invention, the non-aqueous solvent is present at about 50 mg/mL to 100 mg/mL, 50 mg/mL to 200 mg/mL, 50 mg/mL to 250 mg/mL, 50 mg/mL to 300 mg/mL, 100 mg/mL to 200 mg/mL, 100 mg/mL to 250 mg/mL, 100 mg/mL to 300 mg/mL, 200 mg/mL to 250 mg/mL, 200 mg/mL to 300 mg/mL, or 250 mg/mL to 300 mg/mL prior to dilution.

In particular embodiments, the non-aqueous solvent is present at a concentration of no more than 30 weight percent (wt. %) of the formulation prior to dilution. In further embodiments, the non-aqueous solvent is present at a concentration of at least 5 weight percent (wt. %) of the formulation prior to dilution. In certain embodiments of the invention the non-aqueous solvent is present at 5-30 weight percent (wt. %) of the formulation prior to dilution. In particular embodiments of the invention the non-aqueous solvent is present at about 10-30 wt. %, 15-30 wt. %, 20-30 wt. %, 25-30 wt. %, 5-28%, 10-28 wt. %, 15-28 wt. %, 20-28 wt. %, 25-28 wt. %, 5-25%, 10-25 wt. %, 15-25 wt. %, 20-25 wt. %, 25-28 wt. %, 5-20%, 10-20 wt. %, 15-20 wt. %, 5-15%, 10-15 wt. %, or 5-10 wt. % prior to dilution.

In particular embodiments, the non-aqueous solvent is present at a concentration of no more than 300 μL/mL prior to dilution. In further embodiments, the non-aqueous solvent is present at a concentration of at least 50 μL/mL prior to dilution. In certain embodiments of the invention, the non-aqueous solvent is present at a concentration of about 50 μL/mL to 300 μL/mL. In further embodiments of the invention, the non-aqueous solvent is present at about 50 μL/mL to 100 μL/mL, 50 μL/mL to 200 μL/mL, 50 μL/mL to 250 μL/mL, 50 μL/mL to 275 μL/mL, 50 μL/mL to 300 μL/mL, 100 μL/mL to 200 μL/mL, 100 μL/mL to 250 μL/mL, 100 μL/mL to 275 μL/mL, 100 μL/mL to 300 μL/mL, 200 μL/mL to 250 μL/mL, 200 μL/mL to 300 μL/mL, or 250 μL/mL to 300 μL/mL prior to dilution.

In certain embodiments, water is present at a concentration of at least about 500 μL/mL prior to dilution. In other embodiments of the invention, water is present at a concentration of at least about 600 μL/mL, 750 μL/mL, or 950 μL/mL prior to dilution. In further embodiments of the invention, water is present at a concentration of about 500 µL/mL to 950 µL/mL prior to dilution. In still further embodiments of the invention, water is present at about 500 µL/mL to 800 µL/mL, 500 µL/mL to 700 µL/mL, 500 µL/mL to 600 µL/mL, 600 µL/mL to 750 µL/mL, 600 µL/mL to 800 µL/mL, 600 µL/mL to 950 µL/mL, 700 µL/mL to 800 µL/mL, 700 µL/mL to 950 µL/mL, or 750 µL/mL to 950 µL/mL prior to dilution.

In particular embodiments, water is present at a concentration of at least about 50 wt. % of the formulation prior to dilution. In further embodiments, water is present at a concentration of at least about 60 wt. %, 75 w t %, or 95 wt. % prior to dilution. In certain embodiments of the invention water is present at a concentration of at least about 50-95 wt. % prior to dilution. of the invention water is present at a concentration of at least about 50-60 wt. %, 50-70 wt. %, 50-80 wt. %, 60-70 wt. %, 60-80 wt. %, 60-95 wt. %, 70-80 wt. %, or 70-95 wt. % prior to dilution In certain embodiments of the invention the formulation is substantially free of anti-oxidants and/or amino acids. In particular embodiments of the invention, the formulation is substantially free of anti-oxidants. In further embodiments of the invention, the formulation is substantially free of chelating agents. As used herein, substantially free of anti-oxidants, amino acids, and/or chelating agents means the formulation does not comprise one or more anti-oxidants, amino acids, and/or chelating agents, at a concentration sufficient to have a stabilizing effect.

In particular embodiments, the formulation is substantially free of additives selected from the group consisting of ascorbic acid and derivatives, tocopherols and derivatives, propyl gallate, thioglycerol, lactobionic acid, methionine, tertiary butylhydroquinone (TBHQ), butylated hydroxyanisole (BHA), butylated hydroxytoluene (BHT), sodium formaldehyde sulfoxylate, sodium hydrogen sulfite, Eethylenediaminetetraacetic acid (EDTA) and derivatives, monoethanolamine gentisate, glutathione, propionic acid, acetone sodium bisulfite, sodium dithionite, citric acid and derivatives, tribasic (tri sodium citrate dihydrate), or suitable mixtures thereof. As used herein, substantially free means the formulation does not comprise one or more additives listed above at a concentration sufficient to have a stabilizing effect.

In particular embodiments of the invention, the formulation comprises tromethamine. In certain embodiments of the invention, the formulation comprises about 12 to 24 mg/mL tromethamine. In further embodiments of the invention, the formulation comprises about 12 to 14 mg/mL tromethamine, about 12 to 16 mg/mL tromethamine, about 14 to 16 mg/mL tromethamine, about 14 to 18 mg/mL tromethamine, about 16 to 18 mg/mL tromethamine, about 16 to 20 mg/mL tromethamine, about 17 to 19 mg/mL tromethamine, about 17 to 21 mg/mL tromethamine, about 18 to 20 mg/mL tromethamine, about 18 to 22 mg/mL tromethamine, about 20 to 22 mg/mL tromethamine, about 20 to 24 mg/mL tromethamine, or about 22 to 24 mg/mL tromethamine. In yet further embodiments of the invention, the formulation comprises about 18 mg/mL tromethamine.

In certain embodiments of the invention, the formulation is not substantially degraded after storage at room temperature for at least about 6 months. In particular embodiments of the invention, the formulation is not substantially degraded after storage at room temperature for at least about 1 year. In further embodiments of the invention, the formulation is not substantially degraded after storage at room temperature for at least about 18 months. In still further embodiments of the invention, the formulation is not substantially degraded after storage at room temperature for at least about 2 years.

In further embodiments of the invention, the formulation is not substantially degraded after storage at 2-8° C. for at least about 6 months. In certain embodiments of the invention, the formulation is not substantially degraded after storage at 2-8° C. for at least about 1 year. In further embodiments of the invention, the formulation is not substantially degraded after storage at 2-8° C. for at least about 18 months. In still further embodiments of the invention, the formulation is not substantially degraded after storage at 2-8° C. for at least about 2 years.

In other embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after storage at room temperature for at least about 6 months, about 12 months, about 18, months, or about 24 months.

In further embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after storage at 2-8° C. for at least about 6 months, about 12 months, about 18, months, or about 24 months.

In still further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after storage at room temperature for at least about 6 months, about 12 months, about 18, months, or about 24 months.

In yet further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after storage at 2-8° C. for at least about 6 months, about 12 months, about 18, months, or about 24 months.

In particular embodiments of the invention, the formulation retains at least about 85% of its initial pemetrexed concentration, at least about 90% of its initial pemetrexed concentration, the formulation retains at least about 92% of its initial pemetrexed concentration, at least about 95% of its initial pemetrexed concentration, the formulation retains at least about 97% of its initial pemetrexed concentration, at least about 98% of its initial pemetrexed concentration, at least about 99% of its initial pemetrexed concentration, at least about 99.5% of its initial pemetrexed concentration, after storage at room temperature for at least about 6 months, about 12 months, about 18, months, or about 24 months.

In further embodiments of the invention, the formulation retains at least about 85% of its initial pemetrexed concentration, at least about 90% of its initial pemetrexed concentration, the formulation retains at least about 92% of its initial pemetrexed concentration, at least about 95% of its initial pemetrexed concentration, the formulation retains at least about 97% of its initial pemetrexed concentration, at least about 98% of its initial pemetrexed concentration, at least about 99% of its initial pemetrexed concentration, at least about 99.5% of its initial pemetrexed concentration, after storage at 2-8° C. for at least about 6 months, about 12 months, about 18, months, or about 24 months.

In certain embodiments of the invention, the formulation is further diluted in a pharmaceutically acceptable diluent. Suitable diluents include, but are not limited to saline, dextrose, water, Ringer's Injection, and Lactated Ringer's Injection. In certain embodiments of the invention, the formulation can be diluted in a calcium containing diluent, such as Ringer's Injection or Lactated Ringer's Injection.

In particular embodiments of the invention, the formulation is diluted in a pharmaceutically acceptable diluent to a suitable initial dosage concentration of pemetrexed. In certain embodiments of the invention the initial dosage concentration of pemetrexed is based on various factors, such as, but not limited to the patient's weight, age, and condition as well as the volume of diluent and can be determined by a practitioner or one of skill in the art. In further embodiments, pemetrexed is diluted to an initial dosage concentration and can be further diluted prior to administration.

In other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its initial dosage concentration of pemetrexed, at least about 97% of its initial dosage concentration of pemetrexed, at least about 98% of its initial dosage concentration of pemetrexed, at least about 99% of its initial dosage concentration of pemetrexed, at least about 99.5% of its initial dosage concentration of pemetrexed, after dilution and storage at about 2° C. to about 8° C. for at least about 12 hours.

In still other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its initial dosage concentration of pemetrexed, at least about 97% of its initial dosage concentration of pemetrexed, at least about 98% of its initial dosage concentration of pemetrexed, at least about 99% of its initial dosage concentration of pemetrexed, at least about 99.5% of its initial dosage concentration of pemetrexed, after dilution and storage at about 2° C. to about 8° C. for at least about 24 hours.

In yet other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its initial dosage concentration of pemetrexed, at least about 97% of its initial dosage concentration of pemetrexed, at least about 98% of its initial dosage concentration of pemetrexed, at least about 99% of its initial dosage concentration of pemetrexed, at least about 99.5% of its initial dosage concentration of pemetrexed, after dilution and storage at about 2° C. to about 8° C. for at least about 48 hours.

In further embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at about 2° C. to about 8° C. for at least about 12 hours.

In other embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at about 2° C. to about 8° C. for at least about 24 hours.

In yet other embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at about 2° C. to about 8° C. for at least about 48 hours.

In still other embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at about 2° C. to about 8° C. for at least about 12 hours.

In further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at about 2° C. to about 8° C. for at least about 24 hours.

In still further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at about 2° C. to about 8° C. for at least about 48 hours.

In other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its dosage concentration of pemetrexed, at least about 97% of its dosage concentration of pemetrexed, at least about 98% of its dosage concentration of pemetrexed, at least about 99% of its dosage concentration of pemetrexed, at least about 99.5% of its dosage concentration of pemetrexed, after dilution and storage at room temperature for at least about 12 hours.

In still other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its dosage concentration of pemetrexed, at least about 97% of its dosage concentration of pemetrexed, at least about 98% of its dosage concentration of pemetrexed, at least about 99% of its dosage concentration of pemetrexed, at least about 99.5% of its dosage concentration of pemetrexed, after dilution and storage at room temperature for at least about 24 hours.

In yet other embodiments of the invention, the formulation retains at least about 85% of its initial dosage concentration of pemetrexed, at least about 90% of its initial dosage concentration of pemetrexed, at least about 92% of its initial dosage concentration of pemetrexed, at least about 95% of its initial pemetrexed concentration, the formulation retains at least about 97% of its initial pemetrexed concentration, at least about 98% of its initial pemetrexed concentration, at least about 99% of its initial pemetrexed concentration, at least about 99.5% of its initial pemetrexed concentration, after dilution and storage at about room temperature for at least about 48 hours.

In further embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at room temperature for at least about 12 hours.

In other embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at room temperature for at least about 24 hours.

In yet other embodiments of the invention, the formulation comprises no more than about 10% w/w impurities, no more than about 8% w/w impurities, no more than about 6% w/w impurities, no more than about 5% w/w impurities, no more than about 4% w/w impurities, no more than about 3.5% w/w impurities, no more than about 3% w/w impurities, no more than about 2.5% w/w impurities, no more than about 2% w/w impurities, no more than about 1.5% w/w impurities, no more than about 1% w/w impurities, no more than about 0.5% w/w impurities, no more than about 0.2% w/w impurities, no more than about 0.1% w/w impurities, after dilution and storage at room temperature for at least about 48 hours.

In further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at room temperature for at least about 12 hours.

In yet further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at room temperature for at least about 24 hours.

In still further embodiments of the invention, the formulation comprises no more than about 10% w/w of the single largest impurity, no more than about 8% w/w of the single largest impurity, no more than about 6% w/w of the single largest impurity, no more than about 5% w/w of the single largest impurity, no more than about 4% w/w of the single largest impurity, no more than about 3.5% w/w of the single largest impurity, no more than about 3% w/w of the single largest impurity, no more than about 2.5% w/w of the single largest impurity, no more than about 2% w/w of the single largest impurity, no more than about 1.5% w/w of the single largest impurity, no more than about 1% w/w of the single largest impurity, no more than about 0.5% w/w of the single largest impurity, no more than about 0.2% w/w of the single largest impurity, no more than about 0.1% w/w of the single largest impurity, after dilution and storage at a room temperature for at least about 48 hours.

In particular embodiments of the invention the formulation is in a vial with a headspace oxygen concentration of less than about 20 v/v %, 18 v/v %, 16 v/v %, 14 v/v %, 12 v/v %, 10 v/v %, 8 v/v %, 6 v/v %, 5 v/v %, 4 v/v %, 3 v/v %, 2 v/v %, or 1 v/v % oxygen.

In certain embodiments of the invention, the formulation is in a single-dose vial. In further embodiments of the invention, the formulation is in a multi-dose vial. In yet further embodiments of the invention, the formulation is in a multi-dose vial intended for use by the same patient. In still further embodiments of the invention, the formulation is in a multi-dose vial intended for use by different patients.

In another embodiment, the invention relates to a method of administering pemetrexed to a patient in need thereof comprising administering an effective amount of a formulation as described herein. In a further embodiment, the invention relates to a method of administering pemetrexed to a patient in need thereof comprising administering an effective amount of a formulation comprising pemetrexed and a non-aqueous solvent present at less than 30 wt %. In a further embodiment, the invention relates to a method of administering pemetrexed to a patient in need thereof comprising administering an effective amount of a formulation comprising pemetrexed and propylene glycol wherein the propylene glycol is present at 5-30 wt %.

EXAMPLES

Example 1: Effect of Non Aqueous Solvents on Pemetrexed Stability

Formulations as described in Table 1 were prepared as follows:

Water for Injection, a suitable base solution (0.1-1 N NaOH or KOH), and citric acid, if present, were combined and mixed to yield a visually uniform mixture. Pemetrexed diacid was incrementally added to the mixture under continuous agitation, and the resulting homogenous suspension was agitated until all solids were completely dissolved. The pH of the solution was adjusted to about 7.4-7.6. Propylene glycol, if present, was then added to the pemetrexed solution, and the mixture was agitated until a visually uniform mixture was obtained. The pH of the solution was adjusted to 7.4-7.6.

|  | B | C | F | I |
|---|---|---|---|---|
| Pemetrexed (diacid) (mg/mL) | 25 | 25 | 25 | 25 |
| Citric Acid•H2O (mg/mL) | 13.2 | 13.2 | — | — |
| Propylene Glycol (µL/mL) | 250 | — | — | 250 |
| NaOH | qs to pH 7.5 | qs to pH 7.5 | qs to pH 7.5 | qs to pH 7.5 |
| Hydrochloric Acid | qs to pH 7.5 | qs to pH 7.5 | qs to pH 7.5 | qs to pH 7.5 |
| WFI | qs | qs | qs | qs |

The stability of Formulations B, C, F, and I was tested under accelerated conditions at 60° C. and 40° C./75% RH over the course of several days. Samples were taken at various time points and diluted with HPLC diluents (60:40 (v/v, Water:ACN)) prior to testing. Impurities were measured by HPLC.

Figure 1B:
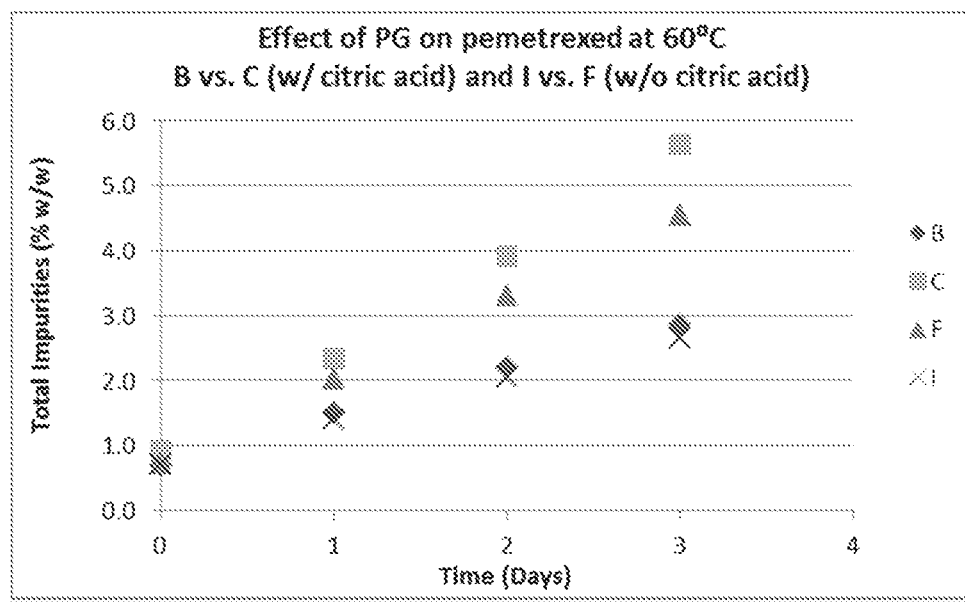
Figure 1C:
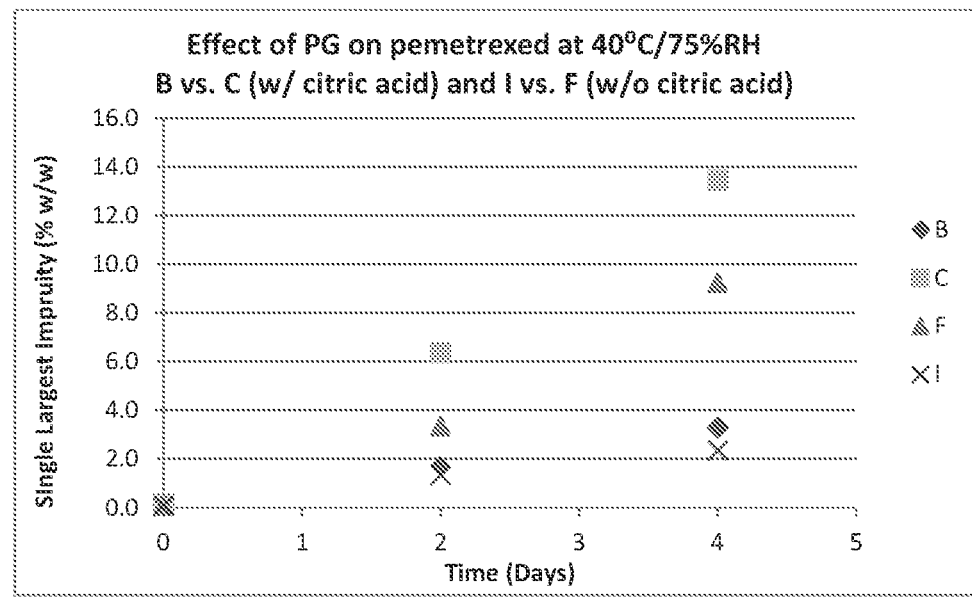
Figure 1D:
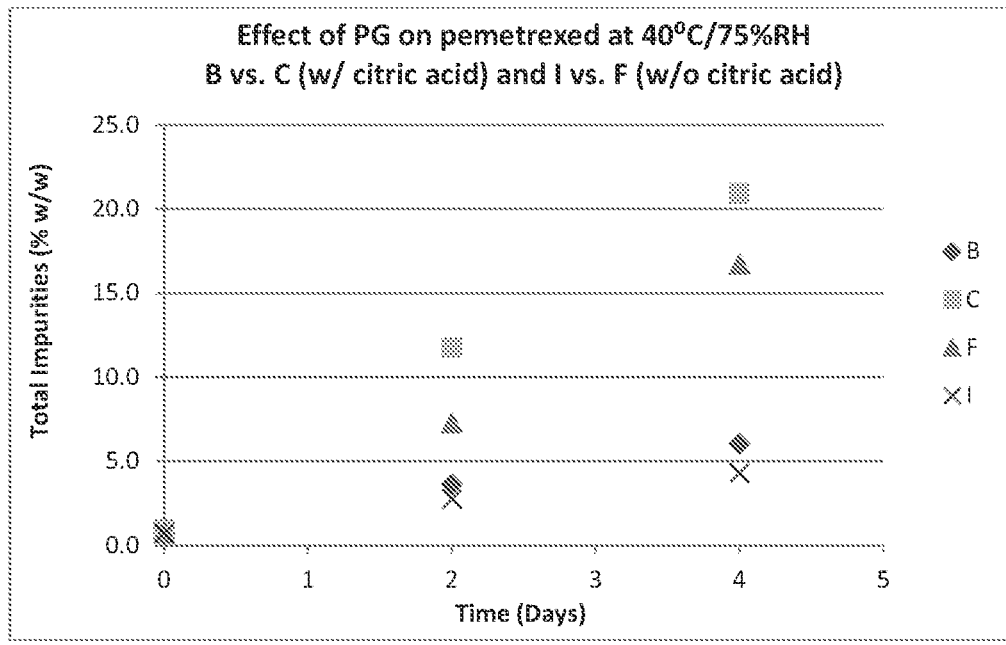

The results are shown in Tables 2A-2D and FIGS. 1A-1D.

TABLE 2A

Single Largest Impurity (% w/w) after storage at 60° C.

|  | B | C | F | I |
|---|---|---|---|---|
| Initial | 0.09 | 0.15 | 0.10 | 0.07 |
| 1 day | 0.61 | 1.26 | 1.00 | 0.56 |
| 2 day | 1.16 | 2.56 | 1.97 | 1.04 |
| 3 day | 1.68 | 4.01 | 2.91 | 1.50 |

TABLE 2B

Total Impurities (% w/w) after storage at 60° C.

| Total Impurity | B | C | F | I |
|---|---|---|---|---|
| Initial | 0.69 | 0.92 | 0.74 | 0.70 |
| 1 day | 1.50 | 2.35 | 2.02 | 1.39 |
| 2 day | 2.20 | 3.93 | 3.31 | 2.04 |
| 3 day | 2.86 | 5.63 | 4.54 | 2.65 |

TABLE 2C

Single Largest Impurity (% w/w) after storage at 40° C./75% RH

| RRT 0.87 | B | C | F | I |
|---|---|---|---|---|
| Initial | 0.09 | 0.15 | 0.10 | 0.07 |
| 2 days | 1.70 | 6.36 | 3.36 | 1.33 |
| 4 days | 3.29 | 13.44 | 9.24 | 2.35 |

TABLE 2D

Total Impurities after (% w/w) storage at 40° C./75% RH

| Total Impurity | B | C | F | I |
|---|---|---|---|---|
| Initial | 0.69 | 0.92 | 0.74 | 0.70 |
| 2 days | 3.63 | 11.75 | 7.28 | 2.75 |
| 4 days | 6.05 | 20.94 | 16.71 | 4.31 |

The long term stability, real-time, and projected, of formulations B, I, and K (See Table 4, prepared as described above) were also measured. Results are shown in Table 3

TABLE 3

Long Term Stability of Pemetrexed Formulations B, I, and K

| | Storage at 2-8 C. (Months) | Single Largest Impurity (% w/w) | Total Impurities (% w/w) | Projected TI in 24 M (% w/w) | Projected SLI in 24 M (% w/w) | Assay (% LC) | pH | Head space oxygen |
|---|---|---|---|---|---|---|---|---|
| Formulation B | 15 | 0.57 | 4.70 | 7.52 | 0.91 | 93.6 | 7.59 | 18.1 |
| Formulation I | 15 | 0.31 | 1.70 | 2.72 | 0.50 | 97.8 | 7.50 | 20.9 |
| Formulation K | 14 | 0.42 | 2.96 | 5.07 | 0.72 | 95.2 | 7.47 | 19.6 |

TABLE 4

Pemetrexed Formulation K

| Ingredient | /mL |
|---|---|
| Pemetrexed diacid | 25.0 mg |
| Propylene Glycol | 250 μL |
| Tromethamine | qs to pH 7.4-7.6 |
| Hydrochloric Acid | qs to pH 7.4-7.6 |
| Water for Injection | qs to 1 mL |

TABLE 6 pH of diluents

| Diluent | pH |
|---|---|
| Normal Saline (NS) | 6.8 |
| Water for Injection (WFI) | 7.01 |
| Ringer's Injection (LR) | 6.6 |
| Lactated Ringer's Injection (LRS) | 6.5 |
| 5% Dextrose in Water (D5W) | 7.5 |

Example 2: Stability of Pemetrexed Formulation K after Dilution

The stability of pemetrexed for up to 48 hours after dilution of Formulation K was evaluated. Normal saline, water for injection and 5% dextrose in water, Ringer's Injection, and Lactated Ringer's Injection were purchased directly and used as is. The pH of each diluent was tested and recorded in Table 6.

Formulation K (25 mg/mL) was diluted to 0.15, 1.5, and 15 mg/mL in the diluents listed above. The mixtures were stored at 2-8° C. and tested at 12, 24, and 48 hours for appearance, assay, impurities, and pH. A sample was taken immediately after dilution for the time zero sample. The 0.15 mg/mL samples were analyzed as is without further dilution, while the 1.5 mg/mL and 15 mg/mL samples were diluted with HPLC diluents (60:40 (v/v, Water:ACN)) prior to testing. Results are in Tables 6 & 7 (each Table represents separate studies).

TABLE 6

Stability of Formulation K after dilution in Normal Saline or Water for Injection

| Diluents | Time (hrs) | Theoretical Pemetrexed conc (mg/mL) | Assay (mg/g) | *Percentage of Theoretical Pemetrexed % | pH | Total Impurity (% w/w) |
|---|---|---|---|---|---|---|
| Bulk Solution | — | 25.0 | 24.80 | 99.2 | 7.50 | 0.16 |
| NS | 0 | | 0.15 | 100.00 | 7.45 | 0.08 |
| | 24 | 0.15 | 0.15 | 100.00 | 7.50 | 0.10 |
| | 48 | | 0.15 | 100.00 | 7.43 | 0.19 |
| | 0 | | 1.52 | 101.54 | 7.40 | 0.12 |
| | 24 | 1.5 | 1.51 | 100.87 | 7.52 | 0.17 |
| | 48 | | 1.50 | 100.20 | 7.52 | 0.16 |
| | 0 | | 14.55 | 98.84 | 7.47 | 0.08 |
| | 24 | 15 | 14.61 | 99.25 | 7.54 | 0.19 |
| | 48 | | 14.71 | 99.93 | 7.58 | 0.17 |
| WFI | 0 | | 0.15 | 100.00 | 7.42 | 0.07 |
| | 24 | 0.15 | 0.15 | 100.00 | 7.53 | 0.04 |
| | 48 | | 0.15 | 100.00 | 7.56 | 0.07 |
| | 0 | | 1.50 | 100.20 | 7.30 | 0.14 |
| | 24 | 1.5 | 1.50 | 100.20 | 7.47 | 0.17 |

TABLE 6-continued

Stability of Formulation K after dilution in Normal Saline or Water for Injection

| Diluents | Time (hrs) | Theoretical Pemetrexed conc (mg/mL) | Assay (mg/g) | *Percentage of Theoretical Pemetrexed % | pH | Total Impurity (% w/w) |
|---|---|---|---|---|---|---|
| | 48 | | 1.51 | 100.87 | 7.50 | 0.16 |
| | 0 | 15 | 14.60 | 99.18 | 7.52 | 0.14 |
| | 24 | | 14.40 | 97.82 | 7.58 | 0.16 |
| | 48 | | 14.70 | 99.86 | 7.59 | 0.11 |

TABLE 7

Stability of Formulation K after dilution in Ringer's Injection, Lactated Ringer's Injection, or 5% Dextrose

| Diluents | Time (hrs) | Theoretical Pemetrexed conc (mg/mL) | Assay (% LC) | *Percentage of Theoretical Pemetrexed % | pH | Total Impurity |
|---|---|---|---|---|---|---|
| Bulk solution | — | 25.0 | 97.6 | NA | 7.37 | 0.35 |
| RS | 0 | 0.15 | 95.4 | 97.8 | 7.23 | 0.41 |
| | 12 | | 95.8 | 98.2 | 7.62 | 0.40 |
| | 24 | | 95.3 | 97.6 | 7.57 | 0.42 |
| | 48 | | 95.4 | 97.8 | 7.72 | 0.44 |
| | 0 | 1.5 | 95.8 | 98.2 | 7.45 | 0.31 |
| | 12 | | 96.2 | 98.6 | 7.53 | 0.34 |
| | 24 | | 95.1 | 97.4 | 7.46 | 0.36 |
| | 48 | | 95.4 | 97.7 | 7.53 | 0.34 |
| | 0 | 15 | 97.8 | 100.2 | 7.47 | 0.35 |
| | 12 | | 98.3 | 100.7 | 7.55 | 0.35 |
| | 24 | | 97.4 | 99.7 | 7.39 | 0.36 |
| | 48 | | 95.6 | 98.0 | 7.53 | 0.33 |
| LRS | 0 | 0.15 | 98.5 | 100.9 | 7.54 | 0.47 |
| | 12 | | 98.9 | 101.3 | 7.45 | 0.55 |
| | 24 | | 98.5 | 100.9 | 7.24 | 0.48 |
| | 48 | | 98.8 | 101.2 | 7.68 | 0.45 |
| | 0 | 1.5 | 98.4 | 100.8 | 7.59 | 0.32 |
| | 12 | | 98.1 | 100.5 | 7.49 | 0.33 |
| | 24 | | 97.4 | 99.8 | 7.33 | 0.34 |
| | 48 | | 98.2 | 100.6 | 7.58 | 0.35 |
| | 0 | 15 | 97.8 | 100.2 | 7.41 | 0.33 |
| | 12 | | 98.3 | 100.7 | 7.58 | 0.32 |
| | 24 | | 98.2 | 100.6 | 7.36 | 0.34 |
| | 48 | | 98.7 | 101.1 | 7.46 | 0.33 |
| D5W | 0 | 0.15 | 97.8 | 100.2 | 7.50 | 0.40 |
| | 12 | | 97.9 | 100.3 | 7.37 | 0.46 |
| | 24 | | 97.7 | 100.1 | 7.34 | 0.58 |
| | 48 | | 97.9 | 100.3 | 7.57 | 0.52 |
| | 0 | 1.5 | 97.0 | 99.4 | 7.39 | 0.31 |
| | 12 | | 96.6 | 99.0 | 7.62 | 0.33 |
| | 24 | | 97.5 | 99.9 | 7.30 | 0.40 |
| | 48 | | 97.2 | 99.6 | 7.53 | 0.39 |
| | 0 | 15 | 97.7 | 100.1 | 7.47 | 0.31 |
| | 12 | | 98.0 | 100.3 | 7.61 | 0.34 |
| | 24 | | 97.9 | 100.3 | 7.40 | 0.32 |
| | 48 | | 98.0 | 100.4 | 7.59 | 0.34 |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, FIGURES and/or drawings, of each and every patent, patent application, and publication cited herein are hereby incorporated herein by reference in their entireties.

What is claimed is:
1. A liquid pharmaceutical composition, consisting of:
20 mg/mL to 30 mg/mL of pemetrexed diacid;
200 mg/mL to 300 mg/mL of propylene glycol;
12 mg/mL to 24 mg/mL of tromethamine;
optionally HCl; and
water,
wherein the pH of the composition is from about 7.4 to 7.6, wherein the composition is suitable for multi-dose administration, and wherein the composition remains stable when stored for about 14 months at a temperature of 2° C. to 8° C. in a container having a head-space oxygen content of about 20% v/v, such that the composition comprises no more than 3% w/w of total impurities after said storage.

2. The liquid pharmaceutical composition of claim 1, consisting of:
    25 mg/mL of the pemetrexed diacid;
    250 mg/mL to 300 mg/mL of the propylene glycol;
    17 mg/mL to 21 mg/mL of the tromethamine;
    optionally HCl; and
    water,
wherein the pH of the composition is from about 7.4 to 7.6.

3. The liquid pharmaceutical composition of claim 1, consisting of:
    25 mg/mL of the pemetrexed diacid;
    250 mg/mL to 300 mg/mL of the propylene glycol;
    18 mg/mL to 20 mg/mL of the tromethamine;
    optionally HCl; and
    water,
wherein the pH of the composition is from about 7.4 to 7.6.

4. A vial containing a liquid pharmaceutical composition consisting of:
    20 mg/mL to 30 mg/mL of pemetrexed diacid;
    200 mg/mL to 300 mg/mL of propylene glycol;
    12 mg/mL to 24 mg/mL of tromethamine;
    optionally HCl; and
    water,
wherein the pH of the composition is from about 7.4 to 7.6, wherein the composition remains stable when stored for about 14 months at a temperature of 2° C. to 8° C. in a container having a head-space oxygen content of about 20% v/v, such that the composition comprises no more than 3% w/w of total impurities after said storage.

5. The vial of claim 4, wherein the vial is a multi-dose vial.

6. The vial of claim 4, wherein the vial contains:
    25 mg/mL of the pemetrexed diacid;
    250 mg/mL to 300 mg/mL of the propylene glycol; and
    17 mg/mL to 21 mg/mL of the tromethamine.

7. The vial of claim 6, wherein the vial is a multi-dose vial.

8. The vial of claim 4, wherein the vial contains:
    25 mg/mL of the pemetrexed diacid;
    250 mg/mL to 300 mg/mL of the propylene glycol; and
    18 mg/mL to 20 mg/mL of the tromethamine.

9. The vial of claim 8, wherein the vial is a multi-dose vial.

* * * * *